United States Patent
Kutzner et al.

(10) Patent No.: US 11,697,809 B2
(45) Date of Patent: Jul. 11, 2023

(54) BIOLOGICAL SYNTHESIS OF AMINO ACID CHAINS FOR PREPARATION OF PEPTIDES AND PROTEINS

(71) Applicant: Christoph Kutzner, Paunzhausen (DE)

(72) Inventors: Christoph Kutzner, Paunzhausen (DE); Marco Giuman, Munich (DE)

(73) Assignee: Christoph Kutzner, Paunzhausen (DE)

(*) Notice: Subject to any disclaimer, the term of this patent is extended or adjusted under 35 U.S.C. 154(b) by 0 days.

(21) Appl. No.: 16/962,065

(22) PCT Filed: Jan. 15, 2019

(86) PCT No.: PCT/EP2019/050892
§ 371 (c)(1),
(2) Date: Jul. 14, 2020

(87) PCT Pub. No.: WO2019/138125
PCT Pub. Date: Jul. 18, 2019

(65) Prior Publication Data
US 2020/0347373 A1    Nov. 5, 2020

(30) Foreign Application Priority Data
Jan. 15, 2018 (DE) .................. 10 2018 200 602.4

(51) Int. Cl.
| | |
|---|---|
| C12P 21/02 | (2006.01) |
| C12P 21/06 | (2006.01) |
| C12N 9/50 | (2006.01) |
| C12N 9/26 | (2006.01) |
| C12N 9/34 | (2006.01) |
| C12N 15/70 | (2006.01) |
| C07K 1/16 | (2006.01) |

(52) U.S. Cl.
CPC ............. *C12N 9/506* (2013.01); *C12N 15/70* (2013.01); *C07K 1/16* (2013.01); *C07K 2319/50* (2013.01); *C07K 2319/70* (2013.01)

(58) Field of Classification Search
None
See application file for complete search history.

(56) References Cited

U.S. PATENT DOCUMENTS

2007/0105192 A1* 5/2007 Villafranca ........... C12P 21/005
                                                                435/85

FOREIGN PATENT DOCUMENTS

| AU | 2011 253 661 A1 | 12/2011 |
|---|---|---|
| EP | 2 746 390 A1 | 6/2014 |
| WO | 2006/113957 A2 | 11/2006 |
| WO | 2008/052387 A1 | 5/2008 |

OTHER PUBLICATIONS

Lin et al., Prot. Exp. Purif. 65:261-266, 2009 (Year: 2009).*
Wu et al., J. Chromatog. B 877:4015-4021,2009 (Year: 2009).*
Achmüller et al., Nat. Methods 4:1037-1043, 2007 (Year: 2007).*
Achmüller et al., "Npro fusion technology to produce proteins with authentic N termini in *E. coli*", Nat. Methods 4:1037-1043 and 13 page Supplementary Information, 2007 (Year: 2007).*
Rappoport et al., Traffic 9:1250-1255, 2008 (Year: 2008).*
International Search Report cited in PCT/EP2019/050892, dated Mar. 6, 2019, 2 pages.
Costa, S. et al., "Fusion tags for protein solubility, purification, and immunogenicity in *Escherichia coli*: the novel Fh8 system", Frontiers in Microbiology, vol. 5, Article 63, S. 1-20, Feb. 2014.
Guillen, D. et al.,"The starch-binding domain as a tool for recombinant protein purification", Appl. Microbial. Biotechnol. 97, S.4141-4148, 2013.
Auer, B. et al.,"Npro autoprotease fusion technology (NAFT), a platform for industrial peptide/protein production in *E. coli*", New Biotechnology, vol. 29, Supplement, p. S240, Sep. 23-26, 2012, Abstract only.
Chong et al., "Single-column purification of free recombinant proteins using a self-cleavable affnity tag derived from a protein splicing element", Gene 192 (1997), pp. 271-281.
Li Y, "Self-cleaving fusion tags for recombinant protein production", Biotechnol Lett. May 2011;33(5):869-81 (Abstract).
Barchiesi et al. , "Functional demonstrations of starch binding domains present in Ostreococcus tauri starch synthases isoforms", BMC Res Notes, 2015, 8:613, 12 pages.
Cockburn et al., "Analysis of surface binding sites (SBSs) in carbohydrate active enzymes with focus on glycoside hydrolase families 13 and 77—a mini-review", Biologia 2014, vol. 69, p. 705-712.
Gilkes et al., "Domains in Microbial ß-1,4-Glycanases: Sequence Conservation, Function, and Enzyme Families", Microbiol Rev 1991, vol. 55, No. 2, 303-315.
Gottipati et al., "The Structure of Classical Swine Fever Virus Npro: A Novel Cysteine Autoprotease and Zinc-Binding Protein Involved in Subversion of Type I Interferon Induction", PLOS Pathog 2013, vol. 9, e1003704, 10 pages.
Meyers et al., "Molecular Cloning and Nucleotide Sequence of the Genome of Hog Cholera Virus", Virology 1989, 171, 555-567.
Paton et al., "Classical swine fever virus: a ring test to evaluate RT-PCR detection methods". Veterinary Microbiology, 73, (2000), pp. 159-174.
Rumenapf et al., "Classical swine fever virus—Alfort/Tuebingen, complete genome", GenBank: J04358.2, Nov. 23, 2005, 5 pages.

* cited by examiner

*Primary Examiner* — David Steadman
(74) *Attorney, Agent, or Firm* — Meunier Carlin & Curfman LLC

(57) ABSTRACT

The invention relates to fusion polypeptides, nucleic acid molecules encoding said fusion polypeptides and genetically modified cells including said nucleic acid molecules. Moreover, the invention relates to a method for preparing target polypeptides using the fusion polypeptides.

10 Claims, 9 Drawing Sheets
Specification includes a Sequence Listing.

BIOLOGICAL SYNTHESIS OF AMINO ACID CHAINS FOR PREPARATION OF PEPTIDES AND PROTEINS

CROSS REFERENCE TO RELATED APPLICATION

This application is a 35 U.S.C. 371 National Phase Entry Application from PCT/EP2019/050892, filed Jan. 15, 2019, which claims the benefit of German Patent Application No. 10 2018 200 602.4 filed on Jan. 15, 2018, the disclosures of which are incorporated herein in their entirety by reference.

The instant application contains a Sequence Listing which has been submitted via EFS-Web and is hereby incorporated by reference in its entirety. Said Sequence Listing, created on Jan. 15, 2018, is named 2923-1363_Sequence Listing.txt and is 21.9 kilobytes in size.

DESCRIPTION

The present invention relates to fusion polypeptides, nucleic acid molecules encoding said fusion polypeptides and genetically modified cells including said nucleic acid molecules. Moreover, the present invention relates to methods for preparing target polypeptides, in particular target peptides having an authentic N-terminus, using the fusion polypeptides.

Naturally occurring and synthetic peptides and polypeptides may be used in various applications such as in the development of active components, in cosmetic and food industry, medicine, agriculture, material research and asymmetric catalysis. Actually, almost each sector of industry preparing or using specialty chemicals is relevant. These numerous functions of peptides are made possible by their high structural and functional diversity.

Thus, there is a high need to develop simple and efficient means as well as methods for preparing peptides.

WO 2006/113957 relates to a method for recombinant preparation of a heterologous polypeptide comprising the expression of a fusion polypeptide, the fusion polypeptide comprising a mutant of the autoprotease $N^{pro}$ of a pestivirus and a second C-terminally connected polypeptide, wherein the second polypeptide may be cleaved autoproteolytically. Moreover, further fusion domains may be present at the N-terminus required for binding to an affinity chromatography system, e.g. poly(amino acids) such as polylysin or epitope tags, i.e. short peptide sequences for which a specific antibody is available.

A severe disadvantage of this method is the need of complex purification steps necessary for collecting the target peptide, such as affinity chromatography and HPLC. Costly reagents (e.g. Ni/NTA, antibodies, Sephadex™, imidazole) and high amounts of polluting and/or toxic solvents are required for affinity chromatography methods. Moreover, compatibility issues of the autoprotease domain have to be considered. Unintended activation of the autoprotease domain during purification can lead to premature cleavage and thus, to yield loss. Moreover, the target peptide characteristics such as the peptide length, polarity and/or toxicity may affect the autoprotease activity and/or the final yield. Further, affinity chromatography purified peptides often need to be purified in an additional HPLC step in order to achieve the desired degree of purity. By this means, the yield is severely reduced and the cost effectiveness of these methods is further limited.

WO 2008/052387 discloses starch-binding domains and recombinant polypeptides including the same, wherein the starch-binding domains are arranged in N-terminal and/or C-terminal direction of the target polypeptide. The fusion polypeptides may be purified by chromatography on a starch carrier.

A severe disadvantage of this method is that the purification domains cannot be cleaved and thus, remain in the target peptide. This modification of the target peptide may lead to unforeseeable and unintended side reactions in the peptide application.

Figure 1:
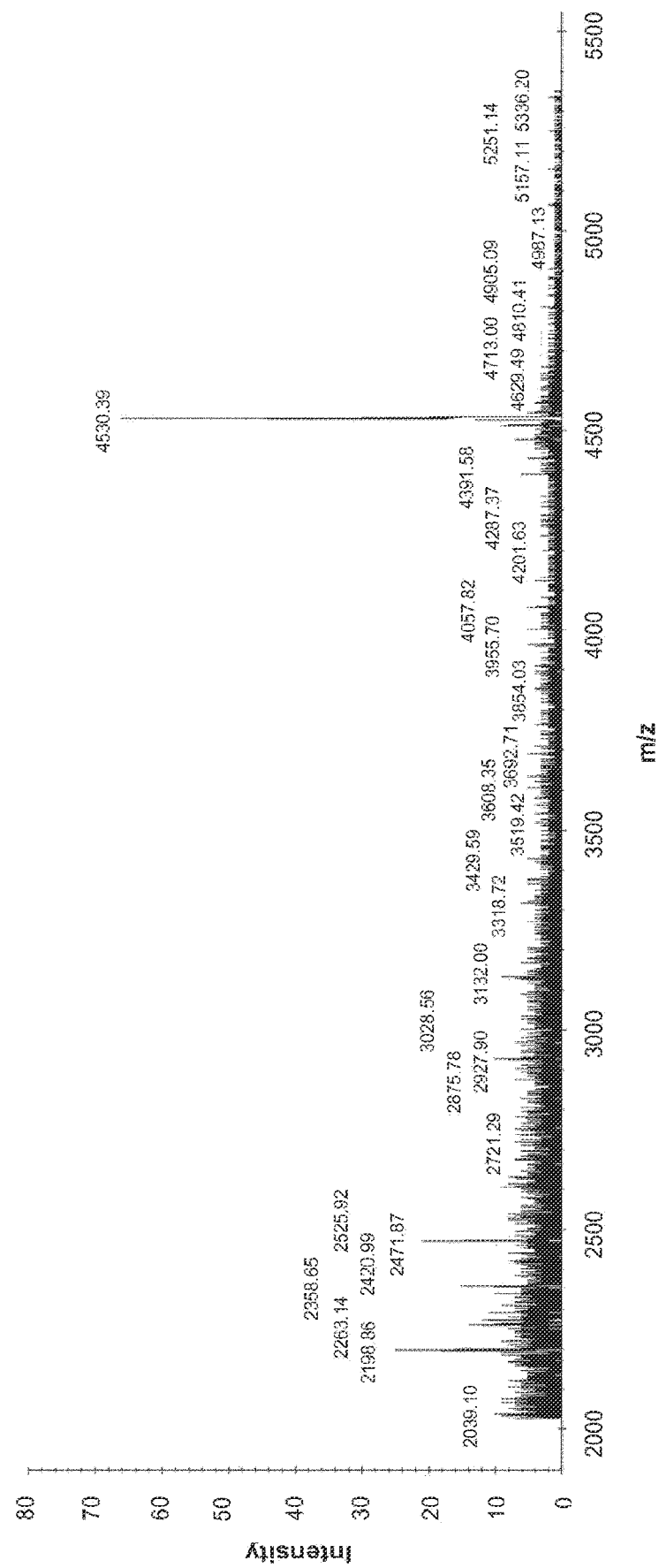
FIG. 1 depicts a MALDI-TOF spectrum of amyloid-β (1-42) oxidized at the methionine residue 35 (+16 Da). The sample was dissolved in acetonitrile/water (1:1, 0.1% trifluoroacetic acid (TFA)) and co-crystallized with 2,5-dihydroxybenzoic acid (DHB) as a matrix (10 mg/ml) in a ratio of 1:50. The measurement was performed at 100 Hz by 1000 laser pulses.

In a first aspect, the present invention relates to a fusion polypeptide comprising in direction from the N-terminus to the C-terminus
(i) a purification domain,
(ii) an autoprotease domain, and
(iii) a target peptide domain, wherein the purification domain (i) binds to a carbohydrate.

In a further aspect, the invention relates to a recombinant nucleic acid molecule encoding a fusion polypeptide as described above, optionally linked to an expression control sequence.

In a still further aspect, the present invention relates to a genetically modified cell including a nucleic acid molecule as described above.

In a still further aspect, the present invention relates to a method for preparing a target peptide comprising the steps of (a) providing a genetically modified cell expressing a fusion polypeptide as described above,
(b) culturing the cell in a suitable culture medium and under conditions suitable for expression of the fusion polypeptide and for formation of inclusion bodies comprising the fusion polypeptide,
(c) solubilizing the inclusion bodies comprising the fusion polypeptide,
(d) contacting the solubilized fusion polypeptide with a carbohydrate-based matrix having affinity to the purification domain (i) under conditions wherein the fusion polypeptide binds to the matrix,
(e) cleaving the fusion polypeptide by the autoprotease domain (ii) and releasing the target peptide (iii), and
(f) collecting the target peptide (iii).

The present invention is based on the finding that the preparation of a target peptide using a fusion polypeptide comprising a carbohydrate-binding purification domain and an autoprotease leads to a significant simplification of the preparation method, e.g. by avoiding complex HPLC purification steps, and/or to an improved yield of an accurately processed target peptide, in particular a target peptide with an authentic N-terminus.

In a preferred embodiment the fusion polypeptide comprises the domains (i), (ii) and (iii) and optionally a N-terminal signal sequence, optionally replacing the start amino acid of the purification domain (i), and/or a linker sequence present between the domains (i) and (ii).

The fusion polypeptide according to the invention comprises (i) a purification domain which binds to a carbohydrate. For example, the purification domain binds to an oligosaccharide or polysaccharide, in particular to cellulose, chitin and/or starch. Preferably, the purification domain (i) has a length of from 25-2000 amino acids, preferably of from 50-1000 amino acids and more preferably of from 70-800 or from 100-600 amino acids.

In a preferred embodiment the purification domain binds to starch. The term "starch" in the sense of the present invention refers to a linear, cross-linked or cyclic carbohydrate of α-1,4- and/or α-1,6-linked glucose units, for example amylase, amylopectin, glycogen, dextrin or cyclodextrin. A purification domain binding to starch comprises, for example, a glucoamylase and/or an amylase and/or a starch-binding domain thereof, for example human amylases, amylase derived from *Aspergillus niger* or glucoamylase derived from *Rhizopus* spp, e.g. the carbohydrate-binding modules CBM20, CBM21 and/or CBM26, or combinations thereof.

An endoglucanase or a cellobiase or a cellulose-binding fragment thereof may e.g. be used as purification domain binding to cellulose. An intein-chitin-binding domain (iCBD) may e.g. be used as purification domain binding to chitin.

In certain embodiments a purification domain (i) according to the present invention has one or more of the following features (a) it binds to starch, such as amylose, amylopectin, glycogen, a dextrin and/or a cyclodextrin;
(b) it contains no, one or more starch-binding domains;
(c) it contains no, one or more surface-binding sites for carbohydrates;
(d) it has no, one or more carbohydrate-binding sites; or
(e) it provides a combination of one or more features of (a)-(d).

The term "starch-binding domain" in the sense of the present invention refers to particular key molecules present in some enzymes and involved in the polysaccharide metabolism. These non-catalytic modules are described to be essential for the binding of starch and for the catalytic activity of starch synthase II (Barchiesi et al., BMC Res Notes 2015, 8, 613).

The term "surface-binding site" in the sense of the present invention refers to a ligand-binding site which is arranged on the catalytic module of an enzyme, but outside the active site. Until now, surface-binding sites have been observed in the crystal structure of more than 45 carbohydrate-active enzymes, wherein approximately half of these enzymes belong to the GH13 family (Cockburn et al., Biologica 2014, 69, 705; Rauter and Lindhorst (Eds.) Carbohydrate Chemistry—Chemical and Biological Approaches—Vol. 39, Specialist Periodical Reports, 2013).

The term "carbohydrate-binding site" in the sense of the present invention refers to a protein domain which is present in carbohydrate-active enzymes such as for example glycoside hydrolases. The majority of these domains has carbohydrate-binding activity. Carbohydrate-binding sites are also referred to as cellulose-binding sites (Gilkes et al., Microbial Rev 1991, 55, 303). Based on amino acid sequence similarity, they are classified in numerous families, more than 65 of which are known until now (Carbohydrate-Active Enzymes database (CAZy) cazypedia.org/index.php/Carbohydate-binding_modules; 10 Jan. or 19 Dec. 2018).

A further element of the fusion polypeptide according to the invention is the autoprotease domain (ii). The term "autoprotease domain" refers to a protease which cleaves a fusion partner that is linked thereto at a predetermined site. The autoprotease domain (ii) can comprise a viral autoprotease, preferably an autoprotease derived from a virus of the family Flaviviridae, more preferably an autoprotease derived from a pestivirus and even more preferably an $N^{pro}$ autoprotease or an active fragment or an active mutant of such an autoprotease. For example, the autoprotease domain (ii) can comprise an $N^{pro}$ autoprotease of CSFV (Classical Swine Fever Virus), e.g. of the CSFV strain Alfort (Gottipati et al., PLoS Pathog 2013, 9, e1003704; Patron et al., Vet Microbial 2010, 73, 137; Meyers et al., Virology 1989, 171, 555; ncbi.nlm.nih.gov/nuccore/J04358, 10 Jan. 2018) or a mutant of an $N^{pro}$ autoprotease. For example, a mutant of an $N^{pro}$ autoprotease may be used wherein at least one cysteine residue of the naturally occurring $N^{pro}$ autoprotease is replaced by another amino acid residue, wherein preferred mutants are described in WO 2006/113957, which is herein incorporated by reference. Preferred mutation sites are C112, C134 and C138 of the naturally occurring $N^{pro}$ autoprotease. A particular preferred embodiment is the mutant EDDIE which is disclosed as SEQ ID NO: 5 in WO 2006/113957, which is herein incorporated by reference. Wild-type $N^{pro}$ autoproteases or $N^{pro}$ autoprotease mutants without mutation of one of the cysteine residues present therein are likewise suitable. Such mutations can comprise a substitution of e.g. at least one basic amino acid by an acidic amino acid, at least one acidic amino acid by a basic amino acid, at least one hydrophobic amino acid by a hydrophilic amino acid and/or at least one hydrophilic amino acid by a hydrophobic amino acid.

The autoprotease domain (ii) may cleave the fusion polypeptide after the autoprotease C-terminus and before the target peptide N-terminus, i.e. before the beginning of the target peptide (iii). Preferably, cleavage occurs such that no amino acid residues of the autoprotease domain (ii) remain with the target peptide (iii) and a target peptide having an authentic N-terminus is obtained. In a further embodiment, a cysteine residue may remain at the N-terminus of the target peptide.

The present invention allows for the purification of various target peptides. The term "target peptide" comprises peptide sequences of 2 or more amino acids in length, e.g. of from 2-1000 or more amino acids. Thus, the target peptide may have, for example, a chain length of (a) 2-100, e.g. 2-50 amino acids, (b) 100-500 amino acids or (c) more than 500 amino acids.

By means of the present invention various types of target peptides may be prepared, in particular peptides that are not or hardly available by common methods such as recombinant synthesis and solid phase synthesis. Peptides according to the invention include for example highly hydrophobic target peptides having an amount of hydrophobic amino acids of ≥10%, preferably ≥20%, more preferably ≥30%, and even more preferably of ≥40% based on the total number of amino acids of the target peptide, wherein hydrophobic amino acids are selected from alanine, valine, leucine, isoleucine, methionine, praline, tryptophan and phenylalanine. On the other hand, highly hydrophilic target peptides may be prepared as well, for example with an amount of hydrophilic amino acids of ≥10%, preferably ≥20%, more preferably ≥30%, even more preferably of 40% based on the total number of amino acids of the target peptide, wherein hydrophilic amino acids are selected from serine, threonine, glutamine, asparagine, tyrosine, glycine, cysteine, glutamic acid, aspartic acid, histidine, arginine and lysine. Moreover, target peptides having a combination of hydrophobic and hydrophilic amino acid blocks as described above can be prepared. For example, those target peptides may have an amount of ≥10%, preferably ≥20%, more preferably ≥30%, even more preferably of ≥40% and up to 100% of hydrophobic amino acids based on the total number of amino acids of the target peptide over longer sections, e.g. sections having a length of preferably 2 to 100 amino acids, of the target peptide, and an amount of ≥10%, preferably ≥20%, more preferably ≥30%, even more preferably ≥40% and up to 100% of hydrophilic amino acids based on the total number of amino acids of the target peptide over further sections, e.g. sections having a length of preferably 2 to 100 amino acids, of the target peptide.

A further aspect of the present invention is a recombinant nucleic acid molecule encoding a fusion polypeptide as described above. The nucleic acid molecule may be present in single-stranded or double-stranded form, e.g. as RNA or DNA. Preferably, the nucleic acid molecule is a double-stranded DNA molecule. Optionally, the nucleic acid sequence encoding the fusion polypeptide is operatively linked to an expression control sequence, e.g. to a promoter and/or enhancer, i.e. a sequence that enables expression in a host cell. For example, the expression control sequence can comprise an autoinducible, chemically and/or thermally inducible promoter which allows for a targeted control of expression.

The nucleic acid molecule may further be arranged on a vector, i.e. a nucleic acid construct which may be introduced in a host cell. Exemplary vectors are viral vectors, plasmids and cosmids suitable for the introduction in a prokaryotic or eukaryotic host cell. Preferably, the vector is a plasmid, in particular a plasmid suitable for the introduction in a prokaryotic host cell.

Optionally, the nucleic acid molecule encoding the fusion polypeptide comprises a signal peptide encoding sequence controlling the type of fusion polypeptide expression in the host cell. Preferably, a signal peptide encoding sequence controlling expression in the form of insoluble inclusion bodies in the host cell is present. An exemplary suitable signal sequence is set forth in SEQ ID NO: 1/SEQ ID NO: 2. Preferably, the signal peptide encoding sequence replaces the start codon of the purification domain (i). Moreover, the recombinant nucleic acid molecule may optionally have a linker encoding sequence between the purification domain (i) and the autoprotease domain (ii). The length of the linker may be 1-50 or more amino acids. In another embodiment, the domains (i) and (ii) are directly fused, i.e. without a linker. In a preferred embodiment, the gene sequence encoding the fusion polypeptide has an additional cloning site, for example a restriction enzyme recognition site, at the 3' terminus of the autoprotease domain (ii). For example, the additional cloning site can be introduced by a silent mutation, i.e. a mutation of the DNA sequence without any impact on the amino acid sequence, and can comprise codons 2 and 3 from direction of the C-terminus of the autoprotease domain, for example. Moreover, the recombinant nucleic acid molecule may include an additional stop codon at the C-terminus, for example the codon TAA.

The genetically modified cell according to the invention includes a nucleic acid molecule as described above, preferably a nucleic acid molecule arranged on a vector, and preferably is able to express the fusion polypeptide, in particular in the form of an insoluble inclusion body, but also in soluble form. The genetically modified cell may be a prokaryotic or eukaryotic cell, preferably a prokaryotic cell, e.g. a gram-negative bacterial cell such as an *E. coli* cell or a gram-positive bacterial cell such as a *Bacillus subtilis* or *Bacillus licheniformis* cell. On the other hand, the cell may also be an eukaryotic cell, for example a yeast cell, an insect cell or a mammal cell.

In a still further aspect, the present invention refers to a method for preparing a target peptide. This method comprises the steps of
(a) providing a genetically modified cell expressing a fusion polypeptide as described above,
(b) culturing the cell in a suitable culture medium and under conditions suitable for expression of the fusion polypeptide and for formation of inclusion bodies comprising the fusion polypeptide,
(c) solubilizing the inclusion bodies comprising the fusion polypeptide,
(d) contacting the solubilized fusion polypeptide with a carbohydrate-based matrix having affinity to the purification domain (i) under conditions wherein the fusion polypeptide binds to the matrix,
(e) cleaving the fusion polypeptide by the autoprotease domain (ii) and releasing the target peptide (iii), and
(f) collecting the target peptide (iii).

Step (a) comprises providing a genetically modified cell expressing a fusion polypeptide. Such cell is obtainable by introducing a nucleic acid molecule including a sequence encoding a fusion polypeptide, in particular in the form of a vector, into the cell by known methods such as for example by transfection or transformation. In step (b), the cell is cultured in a suitable culture medium, e.g. in a culture medium commonly used for the respective cell type. Culturing takes place under conditions wherein expression of the fusion polypeptide and formation of inclusion bodies comprising the fusion polypeptide occurs. For example, an inducible promoter, e.g. an autoinducible, chemically or thermally inducible promoter, may be used to control the expression of the fusion polypeptide. Step (c) comprises solubilizing the inclusion bodies comprising the fusion polypeptide, preferably after being separated from other cellular components. Solubilizing the inclusion bodies may be performed using a buffer containing a high amount of chaotropic substances, such as urea and/or guanidinium hydrochloride.

In step (d), the solubilized fusion polypeptide is contacted with a carbohydrate-based matrix having affinity to the purification domain (i) such that the fusion polypeptide binds to the matrix by its purification domain. For example, chromatography of the fusion polypeptide using the matrix, e.g. using a column containing the matrix, may be performed. This step is performed under conditions wherein the autoprotease domain (ii) is inactive in order to avoid premature cleavage of the target peptide domain (iii). Under these conditions, the amount of cleaved fusion polypeptide is preferably ≥10%, ≥5%, ≥3%, or ≥1%. Conditions under which an "inactive autoprotease domain" is present are (1) conditions wherein the autoprotease domain is constitutionally inactive and is only activated by a change of the environmental conditions, such as by an adaption of the temperature, the pH and/or the ionic strength; or (2) conditions wherein the autoprotease domain is constitutionally active, however, having insufficient activity to achieve a premature cleavage of the target peptide domain during the period of time necessary for performing the method step (d), i.e. is kinetically inactive, e.g. for up to 10 min, up to 20 min, or up to 30 min during which binding of the fusion polypeptide to the matrix and separating of impurities occur.

In a particular embodiment, step (d) is performed under native conditions, i.e. under conditions wherein the autoprotease is constitutionally active. Surprisingly, it was found that even if the fusion polypeptide is present in its native state, the autoprotease domain remains sufficiently inactive during step (d), thus providing conditions under which the fusion polypeptide can be purified on contact with a carbohydrate-based matrix having affinity to the purification domain (i), whilst avoiding yield loss due to an unintended separation of prematurely cleaved target peptide together with impurities. Preferably, an insoluble matrix is used in step (d), which facilitates the separation of impurities.

In step (e), the fusion polypeptide is cleaved by the autoprotease domain (ii) whereby the target peptide (iii) is released. Cleavage of the fusion polypeptide may result from addition of an autoproteolysis buffer, i.e. a buffer providing conditions under which the autoprotease is active, e.g. acidic or alkaline conditions. In one embodiment, cleavage of the fusion polypeptide results from a change of the pH value, for example by addition of an acidic autoproteolysis buffer having a pH of ≥5.0, ≥4.5 or 4.0, or by addition of an alkaline autoproteolysis buffer having a pH of ≥7.0, ≥7.3 or ≥7.5. Under such conditions, a target peptide (iii) with an N-terminal cysteine residue is obtained, in case a fusion polypeptide with a C-terminal cysteine residue in the autoprotease domain (ii) is used.

Finally, in step (f), the target peptide (iii) is collected, preferably comprising a separation from the matrix and the remains of the fusion polypeptide bound thereto and/or an isolation of the target peptide, e.g. by precipitation and/or centrifugation. Preferably, step (f) comprises precipitation of the target peptide in an organic solvent, e.g. an alcohol or a mixture of solvents. Hydrophobic peptides may optionally be extracted with a solvent or a mixture of solvents being non-mixable with water. The collected target peptide may have an authentic N-terminus or an N-terminal cysteine residue.

In a still further aspect, the present invention refers to a method for preparing a target peptide comprising the steps of
  (a') providing a genetically modified cell expressing a fusion polypeptide as described above,
  (b') culturing the cell in a suitable culture medium and under conditions suitable for expression of the fusion polypeptide in soluble form,
  (c') contacting the fusion polypeptide with a carbohydrate-based matrix having affinity to the purification domain (i) under conditions wherein the fusion polypeptide binds to the matrix,
  (d') cleaving the fusion polypeptide by the autoprotease domain (ii) and releasing the target peptide (iii), and
  (e') collecting the target peptide (iii).

Step (a') comprises providing a genetically modified cell expressing a fusion polypeptide. Such cell is obtainable by introducing a nucleic acid molecule including a sequence encoding a fusion polypeptide, in particular in the form of a vector, into the cell by known methods such as transfection or transformation. In step (b') the cell is cultured in a suitable culture medium, e.g. in a culture medium commonly used for the respective cell type. Culturing takes place under conditions wherein expression of the fusion polypeptide in soluble form occurs. For example, an inducible promoter, e.g. an autoinducible, chemically or thermally inducible promoter, can be used in order to control the expression of the fusion polypeptide.

In this embodiment, a fusion polypeptide with an autoprotease domain (ii) being constitutionally inactive under the conditions of expression in the host cell and/or in the culture medium and not being activated until a specific adaption of the environmental conditions, for example being activated by addition of an activating substance and/or adaption of the pH, is preferably used. For example, activation may be performed by adjusting an acidic or alkaline pH as described above.

Steps (c') to (e') may take place in accordance with steps (d) to (f) of the above-described embodiment.

In a still further aspect, the present invention refers to a method for preparing a target peptide comprising the steps of
  (a") providing a genetically modified cell secreting a fusion polypeptide as described above,
  (b") culturing the cell in a suitable culture medium and under conditions suitable for secretion of the fusion polypeptide,
  (c") contacting the fusion polypeptide with a carbohydrate-based matrix having affinity to the purification domain (i) under conditions wherein the fusion polypeptide binds to the matrix,
  (d") cleaving the fusion polypeptide by the autoprotease domain (ii) and releasing the target peptide (iii), and
  (e") collecting the target peptide (iii).

Step (a") comprises providing a genetically modified cell secreting a fusion polypeptide. Such cell is obtainable by introducing a nucleic acid molecule including a sequence encoding a fusion polypeptide and a signal sequence inducing secretion, in particular in the form of a vector, into the cell by known methods such as transfection or transformation. In step (b") the cell is cultured in a suitable culture medium, e.g. in a culture medium commonly used for the respective cell type. Culturing takes place under conditions wherein secretion of the fusion polypeptide occurs. For example, an inducible promoter, e.g. an autoinducible, chemically or thermally inducible promoter, can be used in order to control the secretion of the fusion polypeptide.

In this embodiment, a fusion polypeptide with an autoprotease domain (ii) being constitutionally inactive under the conditions of secretion in the culture medium and not being activated until a specific adaption of the environmental conditions, for example being activated by addition of an activating substance and/or adaption of the pH, is preferably used. For example, activation may be performed by adjusting an acidic or alkaline pH as described above.

Steps (c") to (e") may take place in accordance with steps (d) to (f) of the above-described embodiment.

In a still further aspect, the present invention refers to a recombinant nucleic acid molecule encoding a fusion polypeptide comprising the domains (i) and (ii) as described above and a cloning site for incorporation of a nucleic acid molecule comprising domain (iii) as described above, optionally operatively linked to an expression control sequence. This nucleic acid molecule is a starting material for the preparation of any target peptide, as a nucleic acid molecule encoding such target peptide may be cloned by standard methods such as restriction cleavage and subsequent ligation. This nucleic acid molecule may likewise be arranged on a vector as described above, e.g. a plasmid.

Moreover, the present invention should be described in more detail by the following Examples.

Example 1: Construction of Fusion Polypeptide Encoding Gene Sequences

Gene sequences encoding a fusion polypeptide having three sections were prepared. The N-terminal section consists of a purification domain (i), the middle section consists of an $N^{pro}$ autoprotease domain (ii), and the C-terminal section consists of the target peptide domain (iii). The domains (i) and (ii) are optionally interconnected with a linker (SEQ ID NO: 3/SEQ ID NO: 4).

Human a-amylase (AMY1c; SEQ ID NO: 5/SEQ ID N.: 6), glucoamylase 1 (GA1) derived from *Aspergillus niger* (SEQ ID NO: 7/SEQ ID NO: 8), as well as the carbohydrate-binding units CBM20 (SEQ ID NO: 9/SEQ ID NO: 10) and CBM26 were used as purification domain. $N^{pro}$ (CSFV Alfort 187, SEQ ID NO: 11/SEQ ID NO: 12), as well as the $N^{pro}$ mutant EDDIE (SEQ ID NO: 13/SEQ ID NO: 14) according to WO 2006/113957 were used as autoprotease domain. A methionine-35 oxidized form of amyloid-(1-42), a heptameric valine peptide (Val7), a hydrophobic $Ile1_3Thr_8$ peptide and the known Green Fluorescence Protein (GFP) were used as target peptides.

Example 2: Preparation of Target Peptides

The gene sequences described in Example 1 were expressed in genetically modified host cells.

In a first step, a vector (e.g. the vector pet28a(+)) containing the respective gene sequence was introduced in a host cell, e.g. *E. coli*, BL21 DE 3. The gene sequence is arranged on this vector under control of the isopropyl-β-D-1-thiogalactopyranoside (IPTG) inducible lac promoter. The cells containing the vector were selected, e.g. by plating on kanamycin containing agarose plates. Colonies on this plate were used for the expression.

The bacterial cells were cultured under standard conditions in a suitable culture medium, e.g. LB medium, until an optical density $OD_{600}$ of 0.6 was reached. For this purpose, inducing the gene expression took place at 37° C. for a period of 12 h by addition of IPTG (1 mM final concentration).

Following expression the cells were harvested by centrifugation, mixed with a lysis buffer (e.g. 2 mM $MgCl_2$, 5 mM EDTA, 75 mM NaOAc, 20 mM HEPES pH 7.3) and disrupted by sonification. The fusion polypeptide was produced during the expression phase in the form of inclusion bodies (IBs) inside the cells and thus, was present in an insoluble and crystalline form within the cells. Then, the IBs were solubilized in a solubilizing buffer (e.g. 8 M urea, 6 M guanidinium HCl, 20 mM HEPES, 50 mM dithiothreitol pH 7.3), preferably under reducing conditions to be further processed. 10-30 ml of buffer were used for the cell mass derived from 1 l of culture.

In the denaturation buffer the autoprotease domain of the fusion polypeptide is inactive. For conversion into the native conformation and thus, for purification and activation of the autoprotease the solution of the solubilized IBs was added to a suspension of an autoproteolysis buffer (e.g. 0.5 M arginine, 100 mM HEPES, 10 mM sucrose, 5 mM EDTA pH 7.3) and starch, e.g. corn starch. Other sources of starch are likewise suitable. In doing so, the fusion protein was bound to the starch by its purification domain (amylase, glucoamylase or starch-binding domain).

Then, the fusion protein was incubated in the suspension of autoproteolysis buffer and starch for 10 min at 37° C. under constant agitation. Subsequently, the suspension was centrifuged and the supernatant was decanted. The centrifugate was resuspended in water for two or more times and re-centrifuged. The respective supernatants were discarded. By this means, possible impurities were removed. As a next step, the centrifugate was resuspended in autoproteolysis buffer and was stored at 8° C. for 60 min. After resuspension and subsequent centrifugation the supernatant was precipitated in alcohol and again centrifuged. By this means, a target peptide was obtained which may be lyophilized and thus be made storable.

In case the target peptide is a water-insoluble peptide or protein (e.g. amyloid-μ-peptide), the starch was re-extracted in a suitable solvent (such as hexafluoroisopropanol, HFIP) prior to precipitation in alcohol, centrifuged and subsequently precipitated.

Example 3: Characterization of the Target Peptides

The identity of the target peptides obtained in Example 2 was verified by spectroscopic and spectrometric methods.

FIG. 1 depicts a MALDI-TOF spectrum of amyloid-(1-42) oxidized at the methionine residue 35 (+16 Da). The sample was dissolved in acetonitrile/water (1:1, 0.1% trifluoroacetic acid (TFA)) and co-crystallized with 2,5-dihydroxyenzoic acid (DHB) as a matrix (10 mg/ml) in a ratio of 1:50. The measurement was performed at 100 Hz by 1000 laser pulses.

Figure 2:
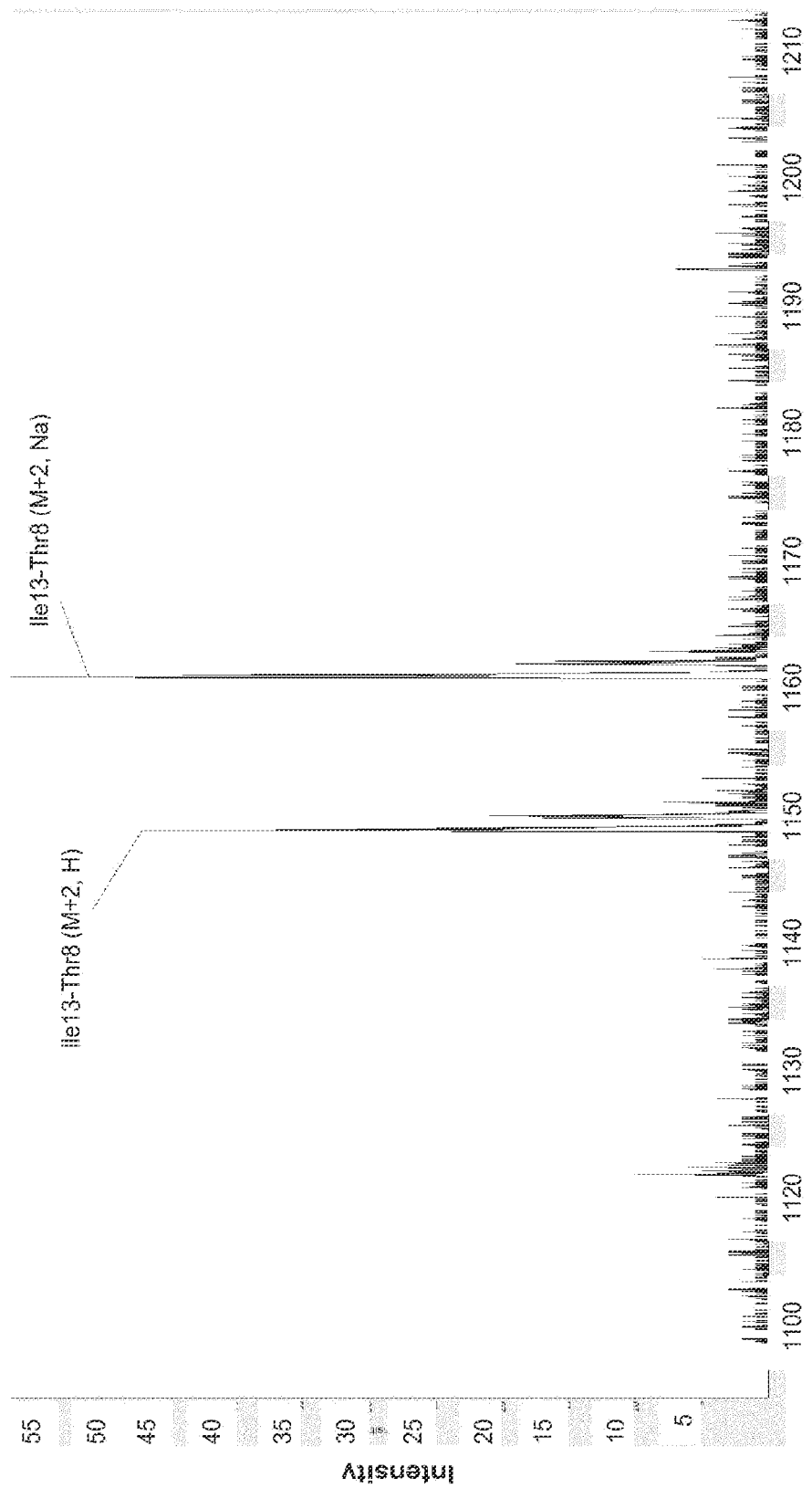
FIG. 2 depicts a MALDI-TOF spectrum of Ile13Thr8. The sample was dissolved in acetonitrile/water 1:1, 0.1% TFA and co-crystallized with DHB as a matrix (10 mg/ml) in a ratio of 1:50. The measurement was performed at 100 Hz by 1000 laser pulses. Two signals were detected corresponding to Ile13Thr8 (M/Z=2) and Ile13Thr8+Na (M/Z=2).

FIG. 2 depicts a MALDI-TOF spectrum of Ile13Thrs. The sample was dissolved in acetonitrile/water 1:1, 0.1% TFA and co-crystallized with DHB as a matrix (10 mg/ml) in a ratio of 1:50. The measurement was performed at 100 Hz by 1000 laser pulses. Two signals were detected corresponding to $Ile_{13}Thr_8$ (M/Z=2) and $Ile_{13}Thr_8$+Na (M/Z=2).

Figure 3:
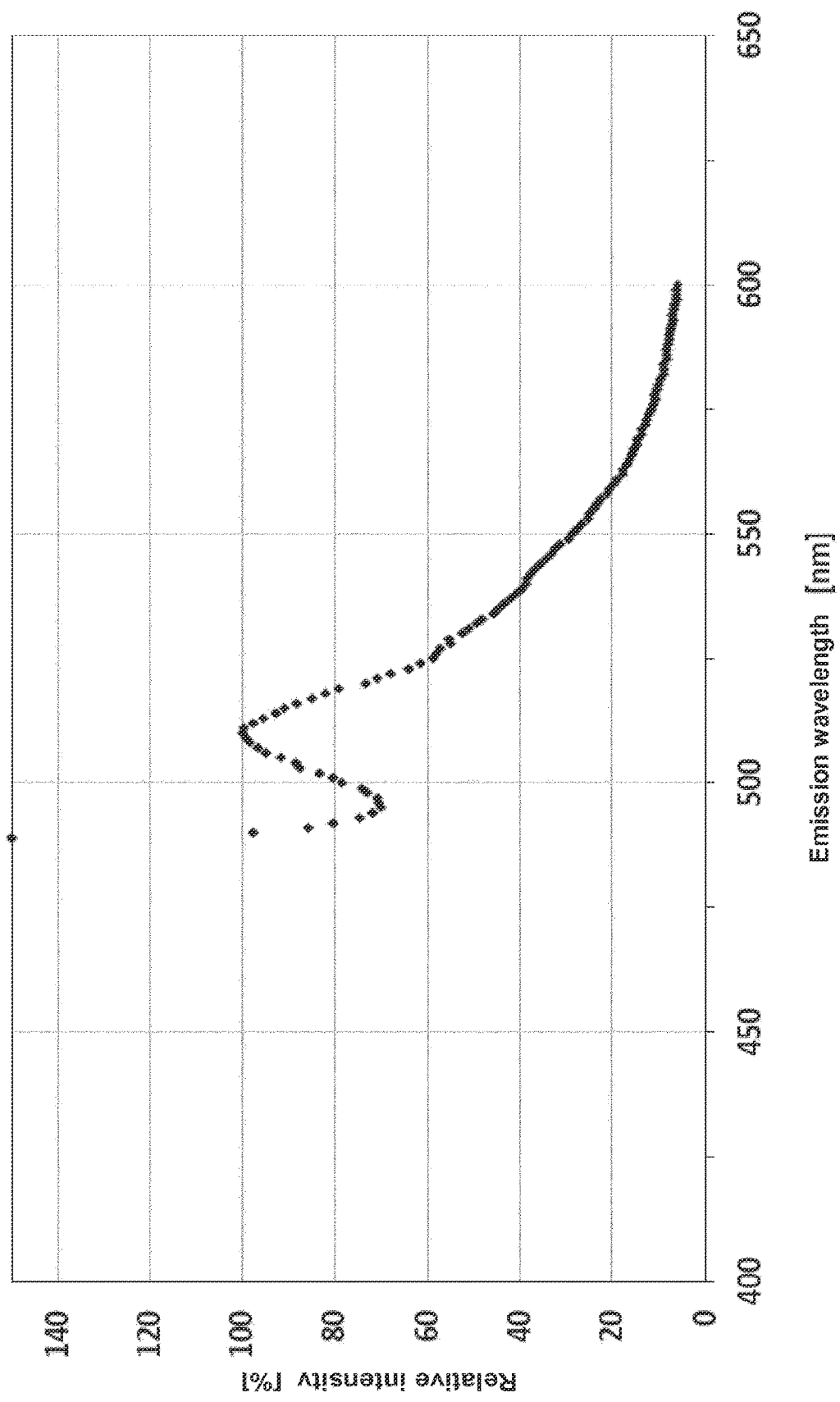
FIG. 3 depicts a fluorescence emission spectrum of GFP at an excitation wavelength of 485 nm and a detected emission wavelength of 510 nm.

FIG. 3 depicts a fluorescence emission spectrum of GFP at an excitation wavelength of 485 nm and a detected emission wavelength of 510 nm.

Example 4: Preparation of Target Peptides

Gene sequences according to Example 1 with the target peptide being $Ile_{13}Thr_8$, $Val_7$, melittin or GFP were introduced in host cells and fusion polypeptides were expressed according to Example 2.

Following expression the cells were harvested by centrifugation, resuspended in lysis buffer (e.g. 2 mM $MgCl_2$, 5 mM EDTA, 75 mM NaOAc, 20 mM HEPES pH 7.5) in a ratio of e.g. 1:10 (w/v) and disrupted by sonification. During the expression phase the fusion polypeptides were produced in the form of inclusion bodies (IBs) within the cells. The IBs were solubilized in a solubilizing buffer (e.g. 8 M urea, 6 M guanidinium HCl, 20 mM HEPES, 50 mM dithiothreitol pH 7.5), preferably under reducing conditions to be further processed, for e.g. 40 min at room temperature. 10-30 ml of buffer were used for the cell mass derived from 1 l of culture.

In the solubilizing buffer the autoprotease domain of the fusion polypeptide is inactive. For conversion into the native conformation and thus, for purification and activation of the autoprotease the solution of the solubilized IBs was added to a suspension of an autoproteolysis buffer (e.g. 5 M arginine, 1.7 M HEPES, 1.6 mM sucrose pH 7.5) and starch, e.g. corn starch. Other sources of starch are likewise suitable. In doing so, the fusion protein was bound to the starch by its purification domain (amylase, glucoamylase or starch-binding domain).

Then, the fusion protein was incubated in the suspension of autoproteolysis buffer and starch for 10 min at 37° C. under constant agitation. Subsequently, the suspension was centrifuged and the supernatant was decanted. The centrifugate was resuspended in water for two or more times and re-centrifuged. The respective supernatants were discarded. By this means, possible impurities were removed. As a next step, the centrifugate was resuspended in autoproteolysis buffer (1.2 ml buffer per 100 mg of centrifugate) and stored at 37° C. for 30 min under constant agitation. After subsequent centrifugation the supernatant was precipitated in alcohol, preferably ethanol, and again centrifuged. By this means, a target peptide was obtained which may be lyophilized and thus be made storable.

In case the target peptide is a water-insoluble peptide or protein (e.g. amyloid-β-peptide), the starch was re-extracted in a suitable solvent (such as HFIP) prior to precipitation in alcohol, centrifuged and subsequently precipitated.

Example 5: Characterization of the Target Peptides

The identity of the target peptides obtained in Example 4 was verified by spectroscopic and spectrometric methods.

Figure 4:
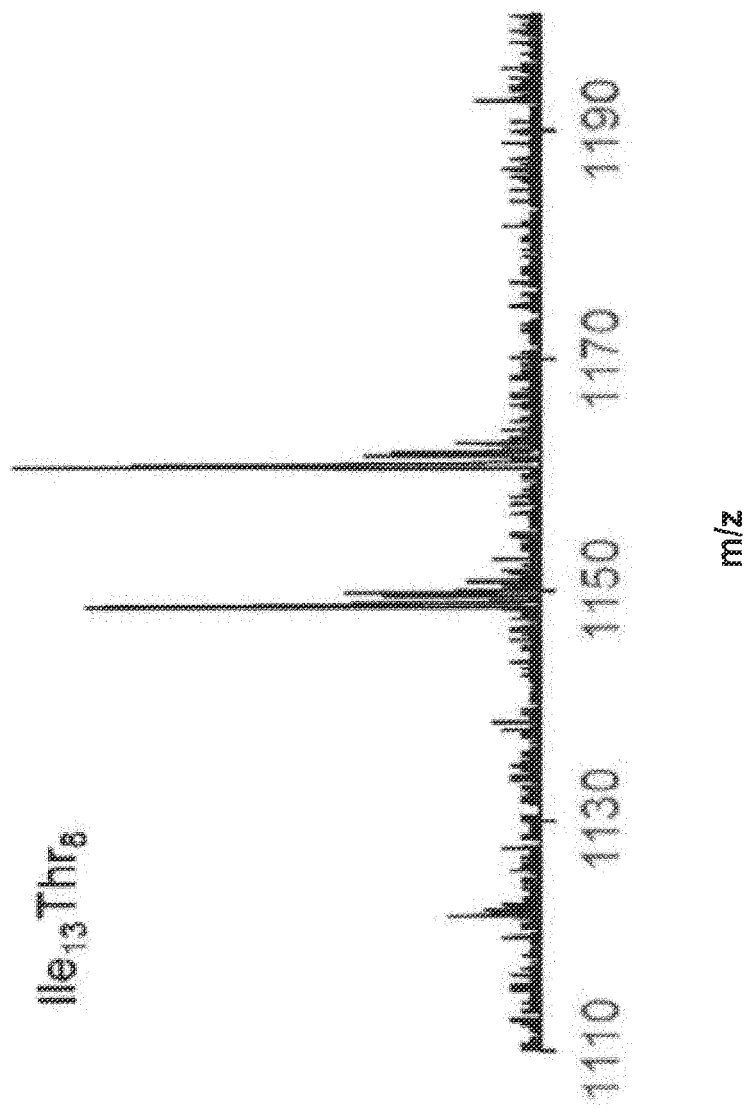
FIG. 4 depicts a MALDI-TOF spectrum of Ile13Thr8. The sample was dissolved in acetonitrile/water 1:1, 0.1% TFA (100 µg/ml) and co-crystallized with DHB as a matrix. The measurement was performed at positive reflector mode. Two signals were detected: m/z=1148 (avg) corresponding to Ile13Thr8 (M+2, H); and m/z=1160 corresponding to Ile13Thr8+(M+2, Na).

FIG. 4 depicts a MALDI-TOF spectrum of $Ile_{13}Thr_8$. The sample was dissolved in acetonitrile/water 1:1, 0.1% TFA (100 μg/ml) and co-crystallized with DHB as a matrix. The measurement was performed at positive reflector mode. Two signals were detected: m/z=1148 (avg) corresponding to $Ile_{13}Thr_8$ (M+2, H); and m/z=1160 corresponding to $Ile_{13}Thr_8$+(M+2, Na).

Figure 5:
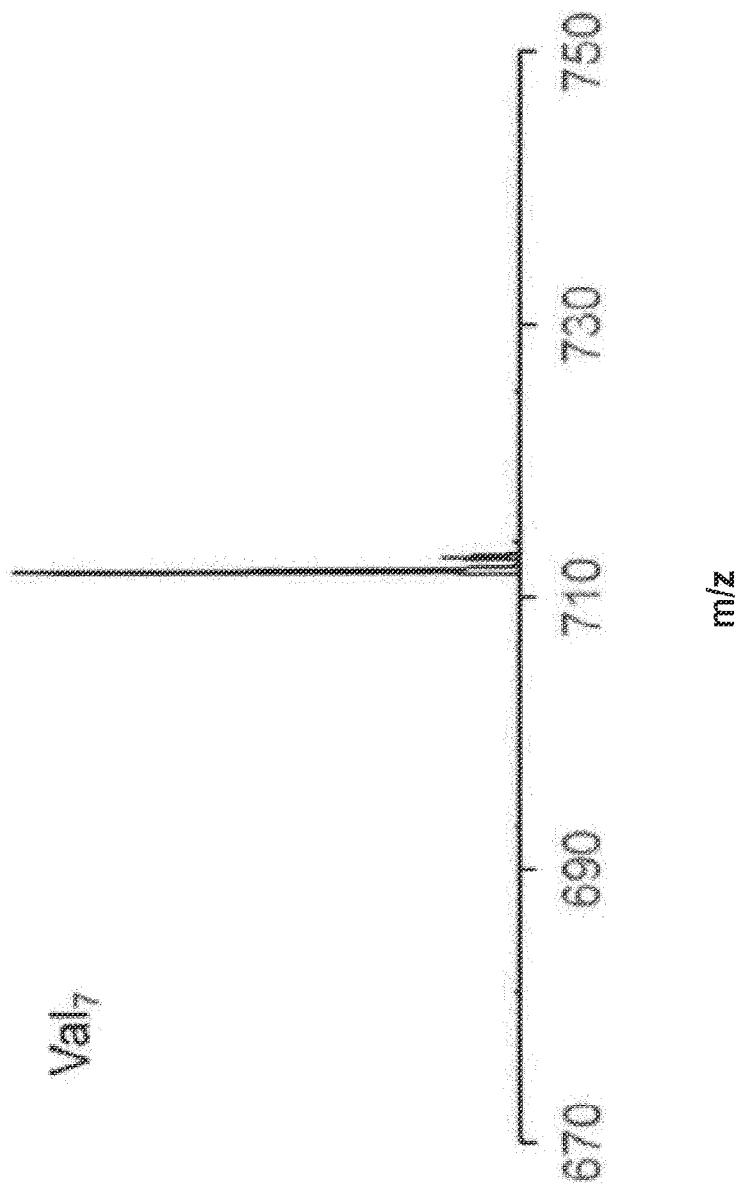
FIG. 5 depicts a MALDI-TOF spectrum of Vale. The sample was dissolved in acetonitrile/water 1:1, 0.1% TFA (100 µg/ml) and co-crystallized with DHB as a matrix. The measurement was performed at positive reflector mode. One signal was detected: m/z=712 (avg) corresponding to Val7 (M+1, H).

FIG. 5 depicts a MALDI-TOF spectrum of Val7. The sample was dissolved in acetonitrile/water 1:1, 0.1% TFA (100 μg/ml) and co-crystallized with DHB as a matrix. The measurement was performed at positive reflector mode. One signal was detected: m/z=712 (avg) corresponding to $Val_7$ (M+1, H).

Figure 6:
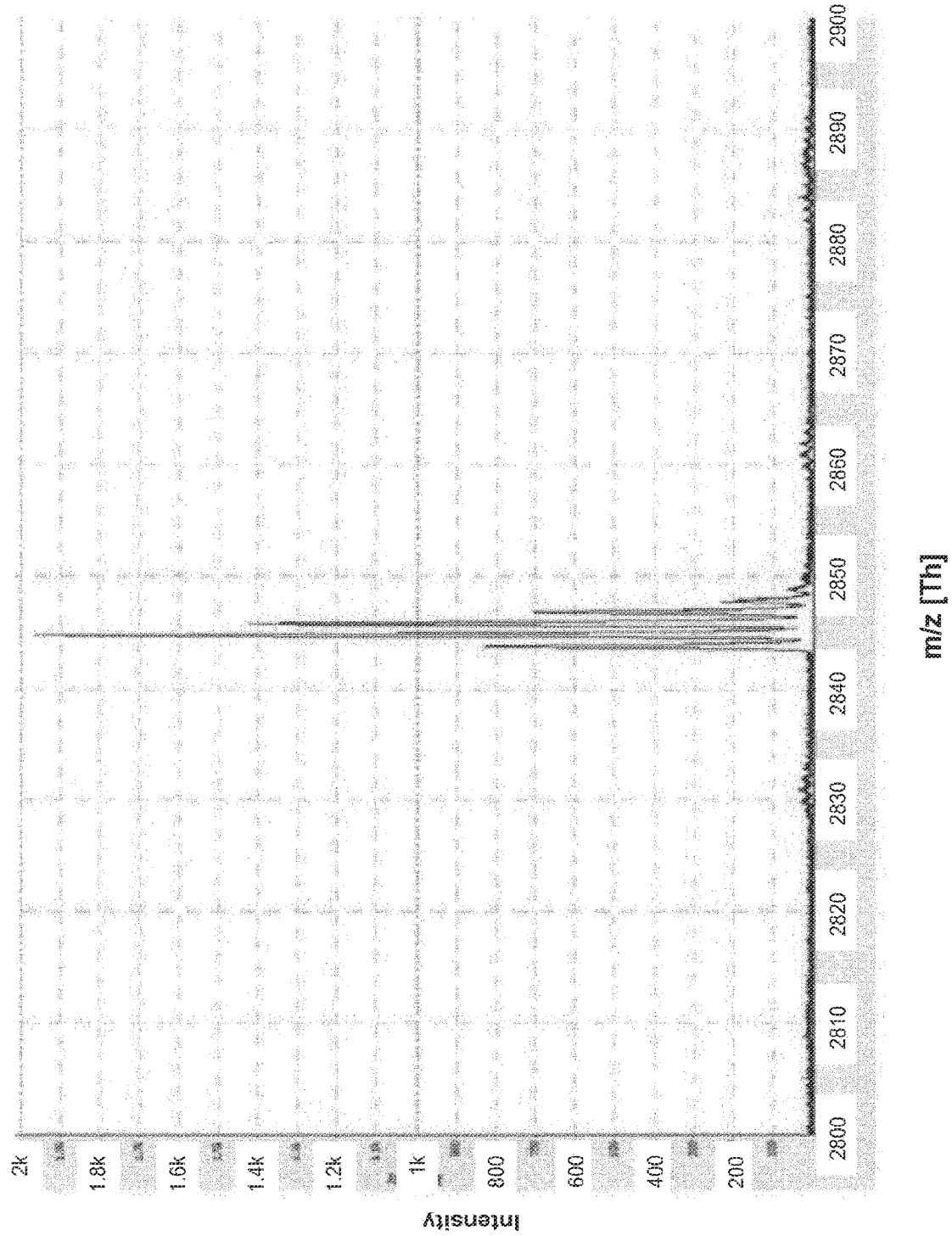
FIG. 6 depicts a MALDI-TOF spectrum of melittin. The sample was dissolved in acetonitrile/water 1:1, 0.1% TFA (100 µg/ml) and co-crystallized with DHB as a matrix. The measurement was performed at positive reflector mode. A single signal was detected: m/z=2843 (avg) corresponding to melittin (M+1, H).

FIG. 6 depicts a MALDI-TOF spectrum of melittin. The sample was dissolved in acetonitrile/water 1:1, 0.1% TFA (100 μg/ml) and co-crystallized with DHB as a matrix. The measurement was performed at positive reflector mode. A single signal was detected: m/z=2843 (avg) corresponding to melittin (M+1, H).

Figure 7:
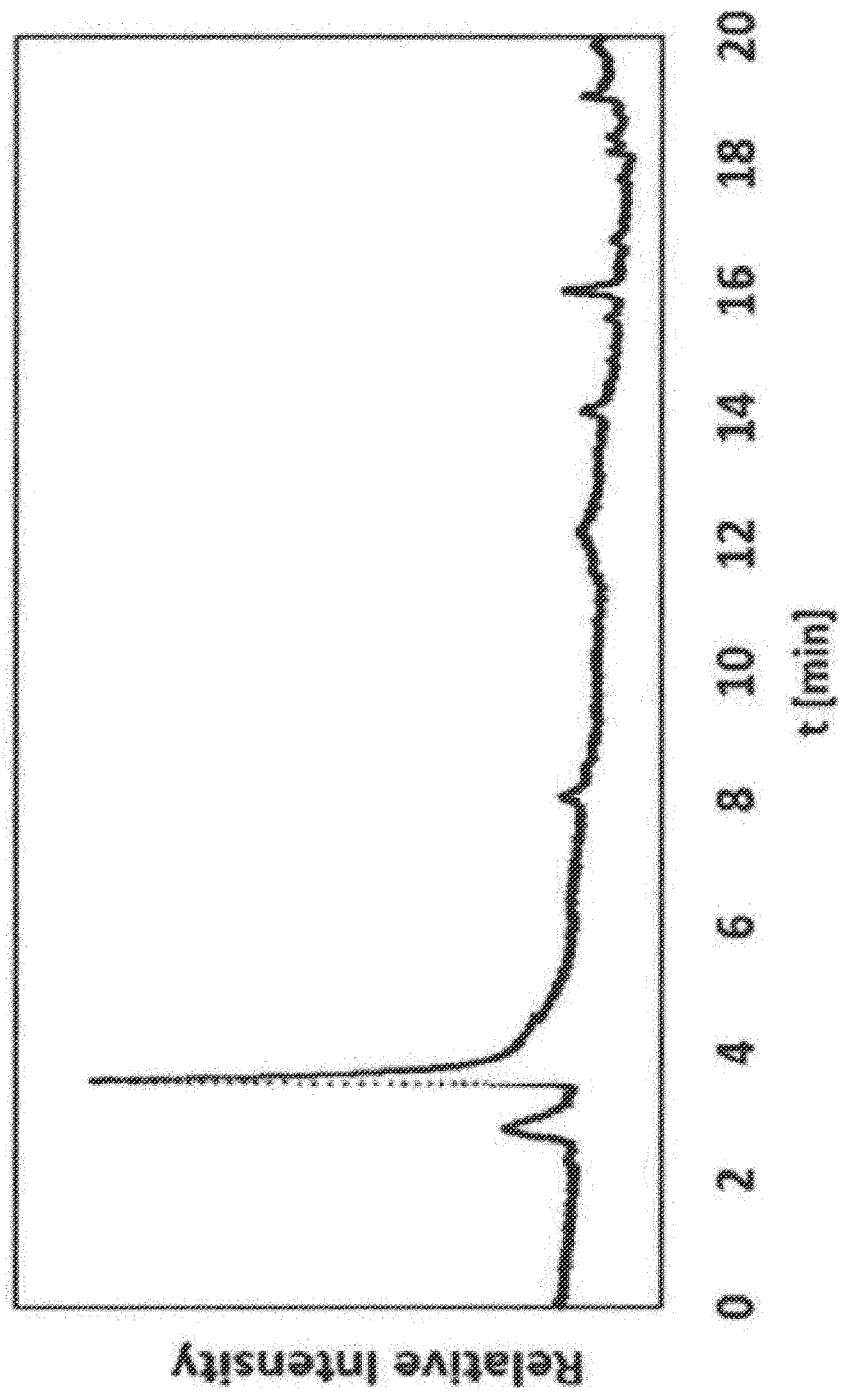
FIG. 7 depicts an UV spectra of melittin at 286 nm (tryptophan) after HPLC purification (flow rate 2 ml/min, linear gradient 5-80% buffer B over 20 min; buffer A: water, 0.1% TFA; buffer B: acetonitrile/water 80:20+0.1% TFA; sample concentration 1 mg/ml)

FIG. 7 depicts an UV spectra of melittin at 286 nm (tryptophan) after HPLC purification (flow rate 2 ml/min, linear gradient 5-80% buffer B over 20 min; buffer A: water, 0.1% TFA; buffer B: acetonitrile/water 80:20+0.1% TFA; sample concentration 1 mg/ml)

Figure 8:
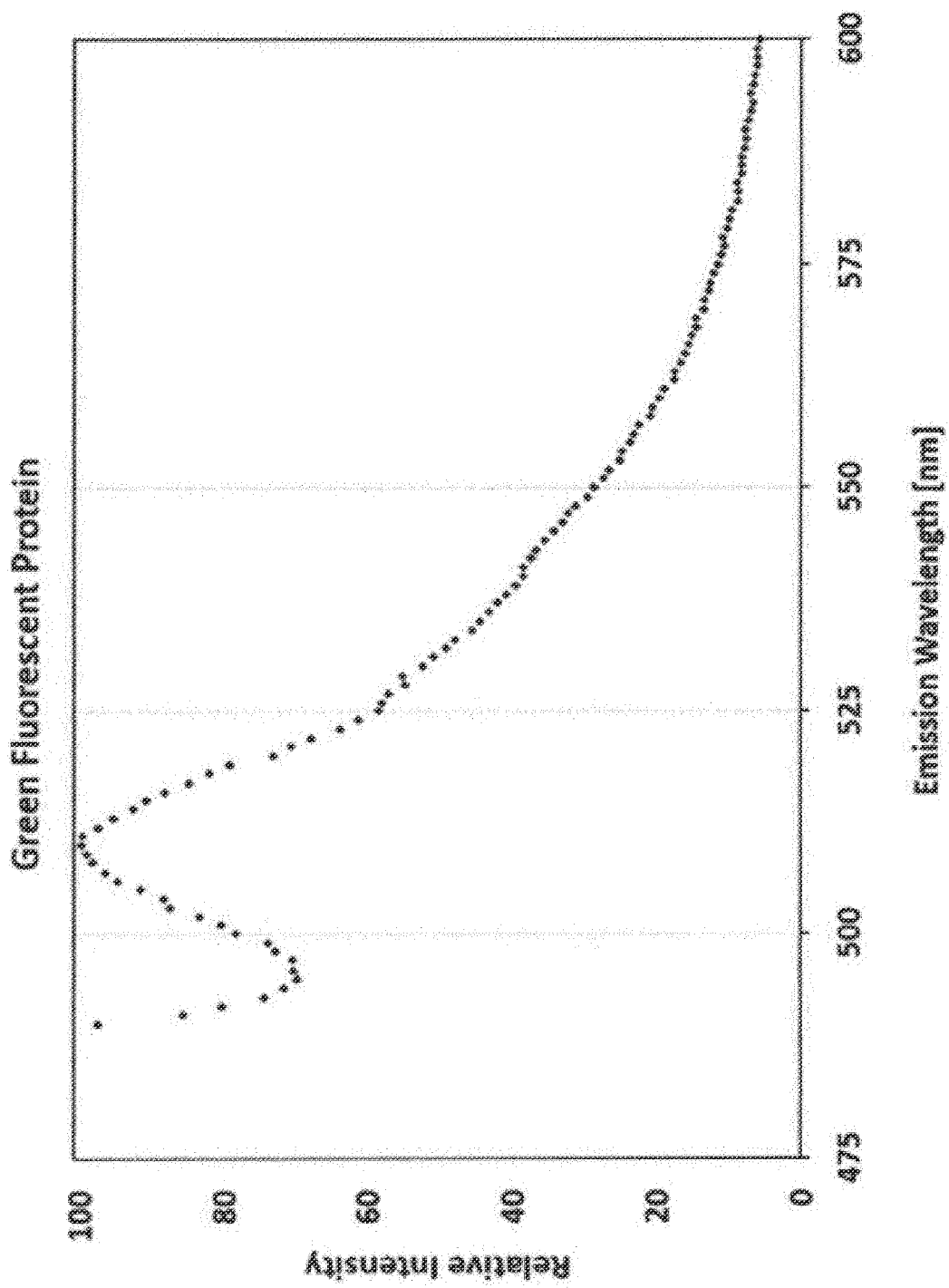
FIG. 8 depicts a fluorescence emission spectrum of GFP (10 mg/ml) at an excitation wavelength of 395 nm. A single emission band was detectable at a wavelength of 509 nm.

FIG. 8 depicts a fluorescence emission spectrum of GFP (10 mg/ml) at an excitation wavelength of 395 nm. A single emission band was detectable at a wavelength of 509 nm.

Figure 9:
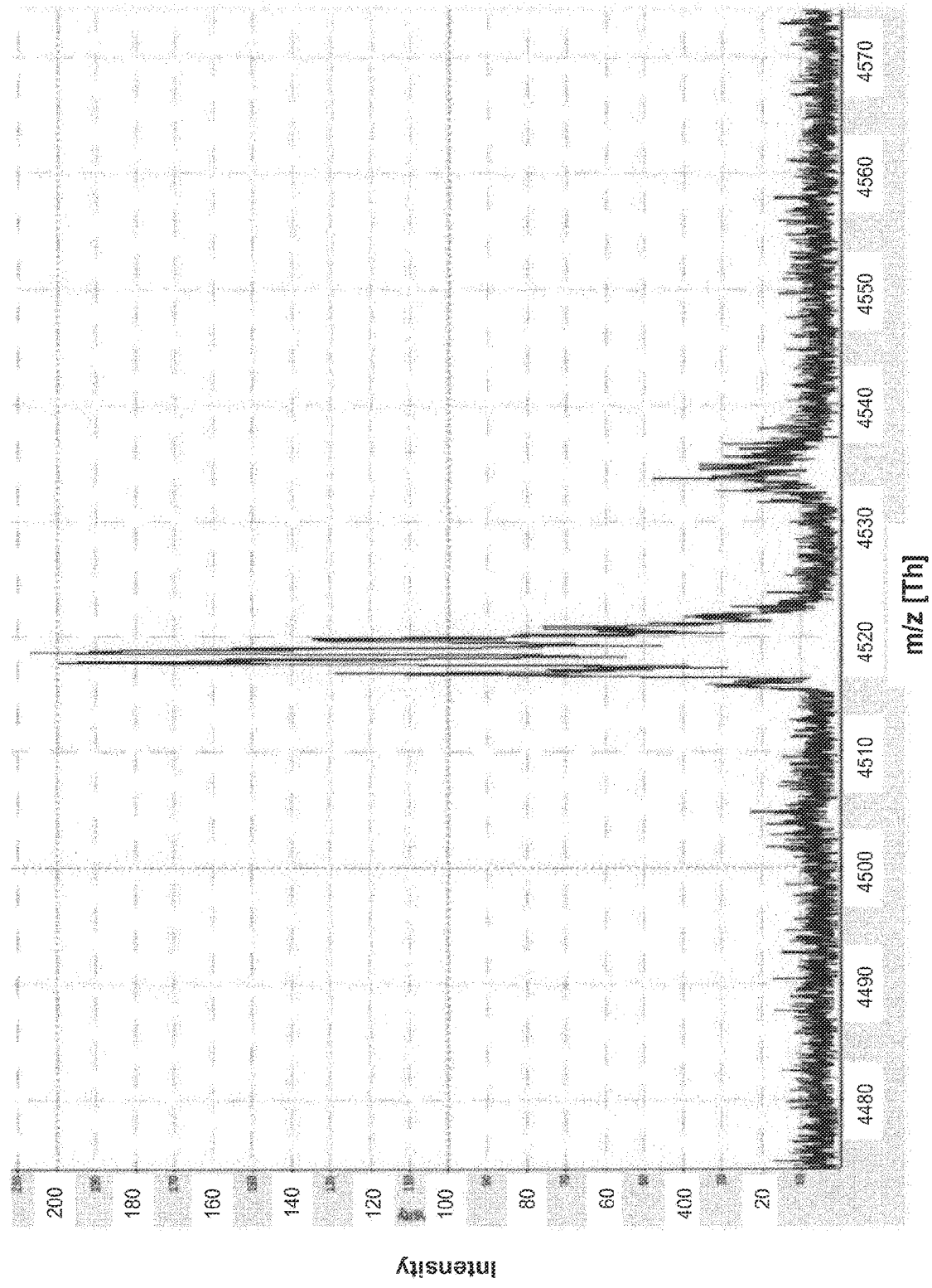
FIG. 9 depicts a MALDI-TOF spectrum of amyloid-β (1-42). The sample was dissolved in acetonitrile/water 1:1, 0.1% TFA (100 µg/ml) and co-crystallized with DHB as a matrix. The measurement was performed at positive reflector mode. A single signal was detected: m/z=4512 (avg) corresponding to amyloid-β (1-42) (M+1, H).

FIG. 9 depicts a MALDI-TOF spectrum of amyloid-β (1-42). The sample was dissolved in acetonitrile/water 1:1, 0.1% TFA (100 μg/ml) and co-crystallized with DHB as a matrix. The measurement was performed at positive reflector mode. A single signal was detected: m/z=4512 (avg) corresponding to amyloid-μ (1-42) (M+1, H).

The invention claimed is:

1. A fusion polypeptide comprising in direction from the N-terminus to the C-terminus:
   (i) a purification domain,
   (ii) an autoprotease domain, and
   (iii) a target peptide domain,
   wherein the purification domain (i) binds to cellulose, chitin, and/or starch and comprises a glucoamylase and/or an amylase, and
   wherein the autoprotease domain (ii) comprises Classical Swine Fever Virus (CSFV) N$^{pro}$ mutant EDDIE, wherein the CSFV N$^{pro}$ mutant EDDIE comprises the amino acid sequence of SEQ ID NO: 14, and wherein the autoprotease domain (ii) cleaves the fusion polypeptide after the C-terminus of the autoprotease domain (ii) and before the N-terminus of the target peptide domain (iii).

2. The fusion polypeptide according to claim 1, wherein the target peptide domain (iii) has a chain length of
   (a) 2-1000 amino acids,
   (b) 100-500 amino acids, or
   (c) more than 500 amino acids.

3. The fusion polypeptide according to claim 1, wherein the target peptide domain (iii) has an amount of
   (a) hydrophobic amino acids of ≥10%,
   (b) hydrophilic amino acids of ≥10%, or
   (c) a combination of (a) and (b).

4. A recombinant nucleic acid molecule comprising a nucleotide sequence encoding the fusion polypeptide according to claim 1, optionally wherein the nucleotide sequence is operatively linked to an expression control sequence.

5. A vector comprising the nucleic acid molecule according to claim 4.

6. An isolated genetically modified cell comprising the recombinant nucleic acid molecule according to claim 4, wherein the cell is a prokaryotic or eukaryotic cell.

7. A method for preparing a target peptide comprising the steps of:
   (a) providing the genetically modified cell according to claim 6,
   (b) culturing the cell in a suitable culture medium and under conditions suitable for expression of the fusion polypeptide and for formation of inclusion bodies comprising the fusion polypeptide,
   (c) solubilizing the inclusion bodies comprising the fusion polypeptide,
   (d) contacting the solubilized fusion polypeptide with a carbohydrate-based matrix comprising cellulose, chitin, and/or starch under conditions wherein the purification domain (i) of the fusion polypeptide binds to the matrix,
   (e) cleaving the fusion polypeptide by the autoprotease domain (ii) and releasing the target peptide (iii), and
   (f) collecting the target peptide (iii).

8. The method according to claim 7, wherein the step (d) comprises chromatography over said matrix.

9. The method according to claim 7, wherein the step (e) occurs due to an addition of autoproteolysis buffer, and/or wherein the step (f) comprises separating and/or isolating the target peptide from the matrix.

10. The method according to claim 7, wherein the target peptide (iii) collected in step (f) has an authentic N-terminus or a cysteine residue at the N-terminus.

\* \* \* \* \*

SEQUENCE LISTING

```
<160> NUMBER OF SEQ ID NOS: 14

<210> SEQ ID NO 1
<211> LENGTH: 117
<212> TYPE: DNA
<213> ORGANISM: Artificial Sequence
<220> FEATURE:
<223> OTHER INFORMATION: Signalsequenz

<400> SEQUENCE: 1
atgaacaaca acgatctgtt ccaagcgagc cgtcgccgct ttctggccca gctgggcggc         60
ctgaccgtgg ctggtatgct gggtccgagc ctgctgacgc cacgtcgcgc aagcgcg          117

<210> SEQ ID NO 2
<211> LENGTH: 39
<212> TYPE: PRT
<213> ORGANISM: Artificial Sequence
<220> FEATURE:
<223> OTHER INFORMATION: Signalsequenz
```

-continued

<400> SEQUENCE: 2

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Ser Ala
        35

<210> SEQ ID NO 3
<211> LENGTH: 75
<212> TYPE: DNA
<213> ORGANISM: Artificial Sequence
<220> FEATURE:
<223> OTHER INFORMATION: Linker

<400> SEQUENCE: 3
ggtagcaaag aatctggcag cgtttctagc gagcagctgg cgcagtttcg tagcctggat    60
gcaggcagcg caagc                                                    75

<210> SEQ ID NO 4
<211> LENGTH: 25
<212> TYPE: PRT
<213> ORGANISM: Artificial Sequence
<220> FEATURE:
<223> OTHER INFORMATION: Linker

<400> SEQUENCE: 4

Gly Ser Lys Glu Ser Gly Ser Val Ser Ser Glu Gln Leu Ala Gln Phe
1               5                   10                  15

Arg Ser Leu Asp Ala Gly Ser Ala Ser
            20                  25

<210> SEQ ID NO 5
<211> LENGTH: 1536
<212> TYPE: DNA
<213> ORGANISM: Homo sapiens

<400> SEQUENCE: 5
atggcgaaac tgttttggct gctgtttacc attggctttt gctgggcgca gtatagcagc    60
aacacccagc agggccgcac cagcattgtg catctgtttg aatggcgctg ggtgatatt    120 gcgctggaat gcgaacgcta tctggcgccg aaaggctttg cggcgtgca ggtgagcccg    180 ccgaacgaaa cgtggcgat tcataacccg tttcgcccgt ggtgggaacg ctatcagccg    240
gtgagctata aactgtgcac ccgcagcggc aacgaagatg aatttcgcaa catggtgacc    300
cgctgcaaca cgtgggcgt gcgcatttat gtggatgcgg tgattaacca tatgtgcggc    360
aacgcggtga gcgcgggcac cagcagcacc tgcggcagct attttaaccc gggcagccgc    420
gattttccgg cggtgccgta tagcggctgg gattttaacg atggcaaatg caaaaacggc    480
agcggcgata ttgaaaacta taacgatgcg acccaggtgc gcgattgccg cctgagcggc    540
ctgctggatc tggcgctggg caaagattat gtgcgcagca aaattgcgga atatatgaac    600
catctgattg atattggcgt ggcgggcttt cgcattgatg cgagcaaaca tatgtggccg    660
ggcgatatta agcgattct ggataaactg cataacctga acagcaactg gtttccggaa    720
ggcagcaaac cgttttattt atcaggaagtg attgatctgg cggcgaacc gattaaaagc    780 agcgattatt ttggcaacgg ccgcgtgacc gaatttaaat atggcgcgaa actgggcacc    840
gtgattcgca atggaacgg cgaaaaaatg agctatctga aaaactgggg cgaaggctgg    900

-continued

```
ggctttatgc cgagcgatcg cgcgctggtg tttgtggata accatgataa ccagcgcggc    960
catggcgcgg gcggcgcgag cattctgacc ttttgggatg cgcgcctgta taaaatggcg   1020
gtgggcttta tgctggcgca tccgtatggc tttacccgcg tgatgagcag ctatcgctgg   1080
ccgcgctatt ttgaaaacgg caaagatgtg aacgattggg tgggcccgcc gaacgataac   1140
ggcgtgacca agaagtgac cattaacccg gataccacct gcggcaacga ttgggtgtgc   1200
gaacatcgct ggcgccagat tcgcaacatg gtgaactttc gcaacgtggt ggatggccag   1260
ccgtttacca actggtatga taacggcagc aaccaggtgg cgtttggccg cggcaaccgc   1320
ggctttattg tgtttaacaa cgatgattgg acctttagcc tgaccctgca gaccggcctg   1380
ccggcgggca cctattgcga tgtgattagc ggcgataaaa ttaacggcaa ctgcaccggc   1440
attaaaattt atgtgagcga tgatggcaaa gcgcatttta gcattagcaa cagcgcggaa   1500
gatccgttta ttgcgattca tgcggaaagc aaactg                            1536
```

<210> SEQ ID NO 6
<211> LENGTH: 512
<212> TYPE: PRT
<213> ORGANISM: Homo sapiens

<400> SEQUENCE: 6

```
Met Ala Lys Leu Phe Trp Leu Leu Phe Thr Ile Gly Phe Cys Trp Ala
1               5                   10                  15

Gln Tyr Ser Ser Asn Thr Gln Gln Gly Arg Thr Ser Ile Val His Leu
            20                  25                  30

Phe Glu Trp Arg Trp Val Asp Ile Ala Leu Glu Cys Glu Arg Tyr Leu
        35                  40                  45

Ala Pro Lys Gly Phe Gly Gly Val Gln Val Ser Pro Pro Asn Glu Asn
    50                  55                  60

Val Ala Ile His Asn Pro Phe Arg Pro Trp Trp Glu Arg Tyr Gln Pro
65                  70                  75                  80

Val Ser Tyr Lys Leu Cys Thr Arg Ser Gly Asn Glu Asp Glu Phe Arg
                85                  90                  95

Asn Met Val Thr Arg Cys Asn Asn Val Gly Val Arg Ile Tyr Val Asp
            100                 105                 110

Ala Val Ile Asn His Met Cys Gly Asn Ala Val Ser Ala Gly Thr Ser
        115                 120                 125

Ser Thr Cys Gly Ser Tyr Phe Asn Pro Gly Ser Arg Asp Phe Pro Ala
    130                 135                 140

Val Pro Tyr Ser Gly Trp Asp Phe Asn Asp Gly Lys Cys Lys Asn Gly
145                 150                 155                 160

Ser Gly Asp Ile Glu Asn Tyr Asn Asp Ala Thr Gln Val Arg Asp Cys
                165                 170                 175

Arg Leu Ser Gly Leu Leu Asp Leu Ala Leu Gly Lys Asp Tyr Val Arg
            180                 185                 190

Ser Lys Ile Ala Glu Tyr Met Asn His Leu Ile Asp Ile Gly Val Ala
        195                 200                 205

Gly Phe Arg Ile Asp Ala Ser Lys His Met Trp Pro Gly Asp Ile Lys
    210                 215                 220

Ala Ile Leu Asp Lys Leu His Asn Leu Asn Ser Asn Trp Phe Pro Glu
225                 230                 235                 240

Gly Ser Lys Pro Phe Ile Tyr Gln Glu Val Ile Asp Leu Gly Gly Glu
                245                 250                 255
```

```
Pro Ile Lys Ser Ser Asp Tyr Phe Gly Asn Gly Arg Val Thr Glu Phe
            260                 265                 270
Lys Tyr Gly Ala Lys Leu Gly Thr Val Ile Arg Lys Trp Asn Gly Glu
        275                 280                 285
Lys Met Ser Tyr Leu Lys Asn Trp Gly Glu Gly Trp Gly Phe Met Pro
    290                 295                 300
Ser Asp Arg Ala Leu Val Phe Val Asp Asn His Asp Asn Gln Arg Gly
305                 310                 315                 320
His Gly Ala Gly Gly Ala Ser Ile Leu Thr Phe Trp Asp Ala Arg Leu
                325                 330                 335
Tyr Lys Met Ala Val Gly Phe Met Leu Ala His Pro Tyr Gly Phe Thr
            340                 345                 350
Arg Val Met Ser Ser Tyr Arg Trp Pro Arg Tyr Phe Glu Asn Gly Lys
        355                 360                 365
Asp Val Asn Asp Trp Val Gly Pro Pro Asn Asp Asn Gly Val Thr Lys
    370                 375                 380
Glu Val Thr Ile Asn Pro Asp Thr Thr Cys Gly Asn Asp Trp Val Cys
385                 390                 395                 400
Glu His Arg Trp Arg Gln Ile Arg Asn Met Val Asn Phe Arg Asn Val
                405                 410                 415
Val Asp Gly Gln Pro Phe Thr Asn Trp Tyr Asp Asn Gly Ser Asn Gln
            420                 425                 430
Val Ala Phe Gly Arg Gly Asn Arg Gly Phe Ile Val Phe Asn Asn Asp
        435                 440                 445
Asp Trp Thr Phe Ser Leu Thr Leu Gln Thr Gly Leu Pro Ala Gly Thr
    450                 455                 460
Tyr Cys Asp Val Ile Ser Gly Asp Lys Ile Asn Gly Asn Cys Thr Gly
465                 470                 475                 480
Ile Lys Ile Tyr Val Ser Asp Asp Gly Lys Ala His Phe Ser Ile Ser
                485                 490                 495
Asn Ser Ala Glu Asp Pro Phe Ile Ala Ile His Ala Glu Ser Lys Leu
            500                 505                 510

<210> SEQ ID NO 7
<211> LENGTH: 1920
<212> TYPE: DNA
<213> ORGANISM: Aspergillus niger

<400> SEQUENCE: 7
atgtccttcc gttccctgct ggcgctgagc ggcctggtgt gcaccggcct ggccaacgtg     60
attagcaaac gcgctacccct ggattcctgg ctgtccaatg aggccactgt tgcgcgtact   120
gcgattctga caatattgg tgctgatggt cgtgggtga cggcgcaga ctctggtatc       180
gtggtggcga gccctagcac cgataatcca gattactttt acacctggac ccgtgattcc   240
ggcctggtcc tgaagacgct ggtagacctg tttcgcaacg cgatacgag cctgctgtct    300
accattgaaa actacattag cgcccaggcc attgttcagg gcatcagcaa tccgagcggt   360
gatctgagct ctggtgctgg tctgggtgaa ccgaagttca atgtggatga aaccgcctac   420
actggtagct ggggtcgccc acaacgtgat ggccctgccc tgcgtgctac cgctatgatt   480
ggtttcggcc aatggctgct ggataatggt tacaccagca ctgctaccga cattgtatgg   540
cctctggttc gcaacgacct gagctatgtc gcccagtatt ggaatcagac gggctatgac   600
ctgtgggaag aggtcaatgg cagctccttc tttaccattg ccgttcaaca tcgtgcgctg   660
gtcgaaggta gcgcatttgc gacggccgta ggtagcagct gcagctggtg cgacagccaa   720
```

-continued

```
gcgccggaaa ttctgtgcta tctgcagtcc ttttggacgg gcagcttcat tctggccaat      780
tttgacagca gccgcagcgg caaagatgca aacacgctgc tgggtagcat ccacaccttt      840
gacccggaag cagcttgcga tgatagcacg tttcaaccgt gctctcctcg tgcgctggcg      900
aaccacaagg aagtggtcga tagctttcgc agcatttaca ccctgaacga tggcctgtct      960
gatagcgaag cggtcgcggt gggtcgttat ccggaagata cgtattacaa cggtaatccg     1020
tggtttctgt gtaccctggc tgcagcggaa caactgtacg atgcgctgta tcaatgggac     1080
aaacagggtt ccctggaggt caccgacgtg agcctggatt tctttaaagc actgtacagc     1140
gatgcggcta ctggtactta tagctccagc agcagcacct atagcagcat gtggatgct      1200
gtgaaaacct ttgcggacgg tttcgtgagc atcgtggaaa cccacgccgc atctaatggt     1260
agcatgagcg agcaatatga taaatccgat ggtgagcagc tgagcgcgcg cgatctgacc     1320
tggtcttatg ccgccctgct gaccgccaac aaccgccgta acagcgttgt gccggcaagc     1380
tggggtgaaa cctctgcgag ctccgtaccg ggtacttgtg cagccaccag cgccattggt     1440
acctacagca gcgttaccgt gacctcttgg ccgagcattg ttgcgactgg cggtactact     1500
acgacggcga cgccaacggg tagcggcagc gtgacgagca cgtctaaaac gacggctacc     1560
gcgtccaaaa ccagcacgag cacgagctcc actagctgta ctaccccgac cgcagtggcg     1620
gtaacttttg acctgaccgc gactacgacc tatggcgaaa acatctacct ggttggctct     1680
attagccagc tgggtgactg ggaaaccagc gatggtattg ccctgagcgc cgacaaatat     1740
accagcagcg atccgctgtg gtatgttacg gtgaccctgc cagcaggcga aagcttcgag     1800
tataaattca tccgcattga atccgatgat agcgtagaat gggaatctga cccgaatcgc     1860
gagtacaccg tgccgcaagc gtgtggtacc agcaccgcca ccgttaccga cacctggcgc     1920
```

<210> SEQ ID NO 8
<211> LENGTH: 640
<212> TYPE: PRT
<213> ORGANISM: Aspergillus niger

<400> SEQUENCE: 8

```
Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160
```

-continued

Gly Phe Gly Gln Trp Leu Leu Asp Asn Gly Tyr Thr Ser Thr Ala Thr
            165                 170                 175

Asp Ile Val Trp Pro Leu Val Arg Asn Asp Leu Ser Tyr Val Ala Gln
        180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
                260                 265                 270

Leu Leu Gly Ser Ile His Thr Phe Asp Pro Glu Ala Ala Cys Asp Asp
            275                 280                 285

Ser Thr Phe Gln Pro Cys Ser Pro Arg Ala Leu Ala Asn His Lys Glu
        290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
                340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Thr Tyr Ser Ser Ile Val Asp Ala Val
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
                420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
                500                 505                 510

Ser Thr Ser Lys Thr Thr Ala Thr Ala Ser Lys Thr Ser Thr Ser Thr
            515                 520                 525

Ser Ser Thr Ser Cys Thr Thr Pro Thr Ala Val Ala Val Thr Phe Asp
        530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Ser Asp Pro Leu Trp Tyr Val Thr Val Thr

```
                        580               585                 590
Leu Pro Ala Gly Glu Ser Phe Glu Tyr Lys Phe Ile Arg Ile Glu Ser
            595                 600                 605

Asp Asp Ser Val Glu Trp Glu Ser Asp Pro Asn Arg Glu Tyr Thr Val
            610                 615                 620

Pro Gln Ala Cys Gly Thr Ser Thr Ala Thr Val Thr Asp Thr Trp Arg
625                 630                 635                 640

<210> SEQ ID NO 9
<211> LENGTH: 336
<212> TYPE: DNA
<213> ORGANISM: Artificial Sequence
<220> FEATURE:
<223> OTHER INFORMATION: CBM20

<400> SEQUENCE: 9
atgtccttcc gttccctgct ggcgctgagc gcggtggcgg tgacctttga tctgaccgcg      60
accaccacct atggcgaaaa catttatctg gtgggcagca ttagccagct gggcgattgg     120
gaaaccagcg atggcattgc gctgagcgcg gataaatata ccagcagcga tccgctgtgg     180
tatgtgaccg tgaccctgcc ggcgggcgaa agctttgaat ataaatttat tcgcattgaa     240
agcgatgata gcgtggaatg ggaaagcgat ccgaaccgcg aatataccgt gccgcaggcg     300
tgcggcacca gcaccgcgac cgtgaccgat acctgg                              336

<210> SEQ ID NO 10
<211> LENGTH: 112
<212> TYPE: PRT
<213> ORGANISM: Artificial Sequence
<220> FEATURE:
<223> OTHER INFORMATION: CBM20

<400> SEQUENCE: 10

Met Ser Phe Arg Ser Leu Leu Ala Leu Ser Ala Val Ala Val Thr Phe
1               5                   10                  15

Asp Leu Thr Ala Thr Thr Thr Tyr Gly Glu Asn Ile Tyr Leu Val Gly
            20                  25                  30

Ser Ile Ser Gln Leu Gly Asp Trp Glu Thr Ser Asp Gly Ile Ala Leu
        35                  40                  45

Ser Ala Asp Lys Tyr Thr Ser Ser Asp Pro Leu Trp Tyr Val Thr Val
    50                  55                  60

Thr Leu Pro Ala Gly Glu Ser Phe Glu Tyr Lys Phe Ile Arg Ile Glu
65                  70                  75                  80

Ser Asp Asp Ser Val Glu Trp Glu Ser Asp Pro Asn Arg Glu Tyr Thr
                85                  90                  95

Val Pro Gln Ala Cys Gly Thr Ser Thr Ala Thr Val Thr Asp Thr Trp
            100                 105                 110

<210> SEQ ID NO 11
<211> LENGTH: 504
<212> TYPE: DNA
<213> ORGANISM: pestivirus

<400> SEQUENCE: 11
atggaattga atcatttcga gttgctatat aagacgaaca agcaaaagcc cgttggcgtg      60
gaggaacccg tgtacgatga aaccggaaaa cctctgttcg agacccatc ggaagtacac      120 cctcagagta ctctgaaact tccacatgac cgagggcgcg gcaacattaa acgaccctc      180 aaaaatttac cgcgcaaagg cgactgtcgt tccgggaacc acctgggtcc agtatctggt     240
```

```
atctacgtta aaccgggccc ggtcttttat caggattaca tgggcccggt ctatcaccgg      300
gccccgctgg agttttttag cgaagcgcag ttttgcgaag tcacaaaacg tatcggccgc      360
gtgaccggct cagatggtcg cctctatcat atctatgtgt gtattgatgg ttgtattctg      420
ctgaaactgg caaaacgtgg tgaaccgcgc actttaaaat ggattcgtaa tttcacggat      480
tgcccgctgt gggttactag ttgc                                             504

<210> SEQ ID NO 12
<211> LENGTH: 168
<212> TYPE: PRT
<213> ORGANISM: pestivirus

<400> SEQUENCE: 12

Met Glu Leu Asn His Phe Glu Leu Leu Tyr Lys Thr Asn Lys Gln Lys
1               5                   10                  15

Pro Val Gly Val Glu Glu Pro Val Tyr Asp Glu Thr Gly Lys Pro Leu
            20                  25                  30

Phe Gly Asp Pro Ser Glu Val His Pro Gln Ser Thr Leu Lys Leu Pro
        35                  40                  45

His Asp Arg Gly Arg Gly Asn Ile Lys Thr Thr Leu Lys Asn Leu Pro
    50                  55                  60

Arg Lys Gly Asp Cys Arg Ser Gly Asn His Leu Gly Pro Val Ser Gly
65                  70                  75                  80

Ile Tyr Val Lys Pro Gly Pro Val Phe Tyr Gln Asp Tyr Met Gly Pro
                85                  90                  95

Val Tyr His Arg Ala Pro Leu Glu Phe Phe Ser Glu Ala Gln Phe Cys
            100                 105                 110

Glu Val Thr Lys Arg Ile Gly Arg Val Thr Gly Ser Asp Gly Arg Leu
        115                 120                 125

Tyr His Ile Tyr Val Cys Ile Asp Gly Cys Ile Leu Leu Lys Leu Ala
    130                 135                 140

Lys Arg Gly Glu Pro Arg Thr Leu Lys Trp Ile Arg Asn Phe Thr Asp
145                 150                 155                 160

Cys Pro Leu Trp Val Thr Ser Cys
                165

<210> SEQ ID NO 13
<211> LENGTH: 504
<212> TYPE: DNA
<213> ORGANISM: Artificial Sequence
<220> FEATURE:
<223> OTHER INFORMATION: Mutante EDDIE

<400> SEQUENCE: 13
atggaactga accattttga actgctgtat aaaaccagca acagaaaacc ggtgggcgtg      60
gaagaaccgg tgtatgatac cgcgggccgc ccgctgtttg caacccgag cgaagtgcat      120 ccgcagagca ccctgaaact gccgcatgat cgcggcgaag atgatattga aaccaccctg      180
cgcgatctgc cgcgcaaagg cgattgccgc agcggcaacc atctgggccc ggtgagcggc      240
atttatatta aaccgggccc ggtgtattat caggattata ccggcccggt gtatcatcgc      300
gcgccgctgg aattttttga tgaaacccag tttgaagaaa ccaccaaacg cattggccgc      360
gtgaccggca gcgatggcaa actgtatcat atttatgtgg aagtggatgg cgaaattctg      420
ctgaaacagg cgaaacgcgg caccccgcgc accctgaaat ggaccccgaa caccaccaac      480
tgcccgctgt gggtgaccag ctgc                                             504
```

```
<210> SEQ ID NO 14
<211> LENGTH: 168
<212> TYPE: PRT
<213> ORGANISM: Artificial Sequence
<220> FEATURE:
<223> OTHER INFORMATION: Mutante EDDIE

<400> SEQUENCE: 14

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Glu Asp Ile Glu Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Thr Gln Phe Glu
            100                 105                 110

Glu Thr Thr Lys Arg Ile Gly Arg Val Thr Gly Ser Asp Gly Lys Leu
        115                 120                 125

Tyr His Ile Tyr Val Glu Val Asp Gly Glu Ile Leu Leu Lys Gln Ala
    130                 135                 140

Lys Arg Gly Thr Pro Arg Thr Leu Lys Trp Thr Arg Asn Thr Thr Asn
145                 150                 155                 160

Cys Pro Leu Trp Val Thr Ser Cys
                165
```